United States Patent [19]

Glick

[11] 4,135,622
[45] Jan. 23, 1979

[54] PACKAGED, DESICCATED SURGICAL ELEMENTS

[75] Inventor: Arthur Glick, New Milford, Conn.

[73] Assignee: American Cyanamid Company, Stamford, Conn.

[21] Appl. No.: 744,365

[22] Filed: Nov. 23, 1976

Related U.S. Application Data

[63] Continuation-in-part of Ser. No. 345,633, Mar. 28, 1973, which is a continuation-in-part of Ser. No. 138,425, Apr. 29, 1971, Pat. No. 3,728,839, which is a continuation-in-part of Ser. No. 788,501, Jan. 2, 1969, abandoned.

[51] Int. Cl.$^2$ .............................................. A61L 17/02
[52] U.S. Cl. .................................... 206/63.3; 206/484
[58] Field of Search ...................... 128/335.5; 206/210, 206/438, 439, 63.3, 484, 363

[56] References Cited

U.S. PATENT DOCUMENTS

| | | | |
|---|---|---|---|
| 3,152,694 | 10/1964 | Nashed et al. | 206/63.3 |
| 3,256,981 | 6/1966 | Kurtz | 206/63.3 |
| 3,297,033 | 1/1967 | Schmitt | 206/63.3 |
| 3,728,839 | 4/1973 | Glick | 53/21 FC |

Primary Examiner—William Price
Assistant Examiner—Joseph Man-Fu Moy
Attorney, Agent, or Firm—Charles F. Costello, Jr.

[57] ABSTRACT

A desiccated, that is, dry absorbable synthetic surgical element of a polymer subject to hydrolytic degradation to non-toxic, tissue-compatible, absorbable components, such as polyglycolic acid suture, is packaged in an airtight sealed container which is substantially impervious to water vapor such as a laminate film having a metallic foil layer. The gaseous contents of the envelope are, prior to sealing the suture within the envelope, either evacuated or replaced with a gas which is inert towards said surgical element and which is substantially free from water. The water content should be below 0.5% by weight of the weight of the surgical element, and preferably is and remains below 0.05% by weight. Desiccated polyglycolic acid sutures and other elements thus packaged retain acceptable levels of strength for at least one year at storage temperatures of 72° F. and ambient humidity outside the package. The contents may be sterilized by using ethylene oxide.

15 Claims, 10 Drawing Figures

PACKAGED, DESICCATED SURGICAL ELEMENTS

CROSS-REFERENCES

This is a continuation-in-part of my copending application Ser. No. 345,633, filed Mar. 28, 1973, which application is a continuation-in-part of copending application Ser. No. 138,425, filed Apr. 29, 1971, now U.S. Pat. No. 3,728,839, filed Apr. 24, 1973, which application is a continuation-in-part of application Ser. No. 788,501, filed Jan. 2, 1969, and abandoned in favor thereof. Another continuation-in-part of Ser. No. 138,425 is now U.S. Pat. No. 3,815,315 of which another continuation-in-part, Ser. No. 459,508, filed Apr. 10, 1974 is now abandoned.

BACKGROUND OF THE INVENTION

Prior to the present invention, virtually all absorbable sutures used in animal and human surgery were prepared from mammalian intestines, such sutures being commonly called catgut sutures. U.S. Pat. No. 3,297,033 describes an absorbable surgical suture made from polyglycolic acid. The disclosure therein is incorporated by reference. This patent in column 3, lines 20 to 53 disclose other components which may be present in the suture. As set forth therein, polyglycolic acid is also properly named as poly(hydroxyacetic acid) or poly-hydroxyacetic ester or polyglycolide and can be considered as essentially a product of polymerization of glycolic acid, that is, hydroxyacetic acid, which in simplified form is shown by the equation:

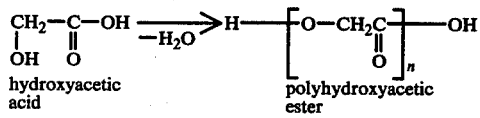

For use as a suture, preferably $n$ is such that the molecular weight is in the range of 10,000 or more. Above 100,000 the polymer is difficult to extrude.

In these molecular weight ranges the polymer has a melt viscosity at 245° C. of between about 400 and about 27,000 poises. Because the fiber is from a synthetic and controllable source, with a controlled molecular weight and is a homopolymer or has a controllable small percentage of comonomer, the absorbability, stiffness and other characteristics can be modified. In general, the higher the molecular weight, the slower the rate of absorption under a given set of conditions.

Among several methods by which polyhydroxyacetic ester can be prepared, one preferred route involves the polymerization of glycolide.

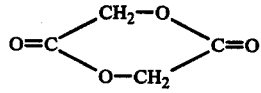

the cyclic dimeric condensation product formed by dehydrating hydroxyacetic acid. During polymerization of glycolide, the ring is broken and straight-chain polymerization occurs. Probably at least a small portion of the polymerization involves the formation of anhydride or ether linkages from a condensation of glycolic acid in a head-to-head, or tail-to-tail direction. The current state of the art is not sufficiently advanced to show with certainty the ratio of anhydride or ether linkages to ester group but indicates these are no more than a few percent of the total. A small quantity of methoxyacetic acid,

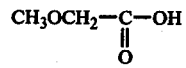

or methyl hydroxyacetic ester,

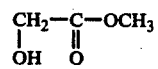

or their homologs, such as higher alkoxyacetic acids, or alkyl hydroxyacetic esters may be present during the polymerization as an end group stabilizer controlling the molecular weight and viscosity. Small quantities of other materials may be present in the chain, as for example d,l-lactic acid, its optically active forms, homologs, and analogs.

Said U.S. Pat. No. 3,297,033 incorporates a reference to U.S. Pat Pat. 2,668,162 — Lowe which quantifies a small amount of lactides as up to 15%, disclosing for example the preparation of a copolymer of 90/10 glycolide/lactide offers two advantages over the homopolymer of glycolide. One advantage is that the melting point of the copolymer is lower than the homopolymer, being in the neighborhood of 200° C.; and the entire reaction can be conducted at approximately the melting point of the copolymer. Operation at the lower temperatures decreases the rate of degradation of the polymer which gives a polymer of lighter color. Another advantage is that the copolymer can be successfully quenched when being extruded into film because the copolymer is less crystalline. On the other hand, the homopolymer shows a greaer tendency to crystallize on extrusion and thereby tends to form opaque areas in the film.

Example 4 of said U.S. Pat. No. 2,668,162 shows reaction conditions.

Surgical elements of polyglycolic acid, including sutures, and other elements mentioned below can be better seen in most surgical fields if the element is colored so as to contrast with blood and tissue or bandages or other background materials.

BRIEF DESCRIPTION OF PRIOR ART

Surgical sutures and other surgical elements containing polymers of glycolic acid are described in:

U.S. Pat. Nos. 3,297,033, 3,463,158, 3,565,077, 3,620,218, 3,626,948, 3,636,956 and 3,728,739.

Reference is made to these patents which show additional prior art and for the definitions therein set forth. Related patents and articles also incorporated herein by this reference on manufacturing of polyglycolic acid and other polymers having glycolic acid ester linkages therein and their properties and use in textile applications and producing surgical elements thereof and their use for surgical purposes are disclosed in:

U.S. Pat. Nos. 2,585,427, 2,658,055, 2,668,167, 2,676,945, 2,758,987, 3,414,939, 3,422,181, 3,435,008, 3,442,871, 3,457,280, 3,468,853, 3,565,869, 3,597,449, 3,597,450, 3,600,223, 3,736,646, 3,737,440, 3,739,773 and 3,781,349.

Belgian Pat. Nos. 776,980, 778,126 and 788,116. British Pat. Nos. 1,332,505, 1,375,008, 1,414,600, 1,428,559, 1,428,560, 1,433,388, 1,448,543, 1,448,544 and 1,450,016.

Swiss Pat. No. 569,485.

Technical Articles: Development of Synthetic Polymer Burn Covering; John B. Gregory et al; DYNATECH R/D COMPANY in conjunction with Department of the Navy, Contract No. N00014-73-C-0201; March 30, 1973.

Development of Synthetic Polymer Burn Covering; John B. Gregory et al; DYNATECH R/D COMPANY in conjunction with Department of the Navy, Contract No. N00014-73-C-0201; June 8, 1973.

Development of a Synthetic Polymer Burn Covering; A. D. Schwope et al; DYNATECH CORPORATION in conjunction with Department of the Navy, Contract Authority NR 104-702/10-3-72 (444); Jan. 31, 1974.

D. E. Cutright et al; Oral Surg., Vol. 31, No. 1, pages 134-139, Jan. 1971; Vol. 32, No. 1, pages 165-173, July 1971; and Vol. 37, No. 1, pages 142-152, Jan. 1974.

Report by R. G. Sinclair and G. W. Gynn entitled Preparation and Evaluation of Glycolic and Lactic Acid Based Polymers for Implant Devices Used in Management of Maxillofacial Trauma; published in conjunction with Contract No. DADA17-72-C-2066; July 25, 1972. Supported by the United States Army Medical Research and Development Command.

Other United States and foreign patents disclose surgical elements in which biodegradability and absorption results from the hydrolytic attack of tissue components on glycolic acid ester linkages in the polymer composing such surgical elements.

Polyglycolic sutures exhibit great uniformity of composition, as compared with catgut. They have excellent package strength, i.e. straight pull and knot pull, and desirable in-vivo strength retention.

It has no been found that the desirable package properties and in-vivo properties of polyglycolic acid surgical elements such as sutures deteriorate when exposed to moisture. Surprising, the exposure of dry polyglycolic acid sutures to small amounts of moisture for very short periods of time is sufficient to cause serious deterioration in the package and in-vivo strength of the sutures on long term standing.

If the polyglycolic acid suture for instance is again dried before packaging, the storage stability is regained. For instance, polyglycolic acid filaments may be braided at ambient temperature and humidity, in a New England climate, and, if the finished braid is dried to remove all absorbed moisture, the dried braid is storage stable. For process uniformity and operator comfort, and air conditioned environment is preferred.

Although the reason for the aforementioned effect of moisture on the properties of polyglycolic acid sutures is not known with certainty, it is believed that several mechanisms may be involved. First, the water may hydrolytically attack the polymer structure to thereby degrade and weaken the polymer. It is also possible that the water may be reacting with unreacted glycolide monomer which can be present in the polymer in an amount up to about 8% to cleave the glycolide ring structure into the linear dimer of glycolic acid which is represented by the following formula:

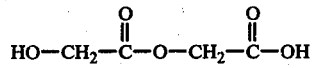

The linear dimer in turn can react with the polymer to break up the high molecular weight polymer into lower molecular weight chains thereby degrading the polymer and causing a reduction in strength. It is also possible that glycolide or the linear dimer of glycolic acid are formed in the polymer as a result of thermal degradation of the polymer which can occur during processing such as, for example, in a high temperature extrusion step.

The exact mechanism of hydrolytic attack is somewhat speculative, and not critical to an explanation or understanding of the present invention. One explanation of the hydrolytic attack is that two glycolic acid units can twist to cause a carbonyl carbon to be sterically approached by the second nearest oxygen in the backbone of the polymer and incipiently form a six membered ring. This anchiomeric attack weakens that carbonyl-oxygen bond, contributing towards hydrolysis of the bond, which thus breaks the polymer chain. [See: Mechanism and Structure in Organic Chemistry, Edwin S. Gould, Holt, Rinehart and Winston, N.Y., 1959, page 562 and reference therein to Winstein, Lindegren, Marshall and Ingraham, J. Am. Chem. Soc. 75, 147 (1953)].

Glycolic acid links in any polymeric chain, particularly those having incipient six membered rings, contribute towards hydrolysis, and fragmentation of the polymer chain into links small enough to be handled by tissue chemistry. The fragmentation is hydrolytic, and does not require an enzyme system. The degradation of catgut requires an enzyme system.

In commercial use, a suture may not be used for months or sometimes years after it is packaged. In the meantime, the suture package may be stored under a variety of environmental conditions. Most of these storage environments expose the package to some moisture. It is mandatory that such sutures be packaged in a material which will prevent permeation of water vapor from the environment surrounding the package through the package and into contact with the suture contained therein. On the other hand, a package material which prevents the entry of water vapor will ordinarily also prevent the exit of water vapor; therefore, any water vapor which is present within the package when it is sealed will remain in the package in intimate contact with the suture. Applicant has further discovered that the exposure of a dry suture to moisture for even extremely brief times (i.e. 20 minutes or less) prior to packaging the suture can have deleterious effects upon the suture when it is packaged in a water impermeable package, especially if the package should happen to be stored at elevated temperatures.

While primarily for sutures, other polyglycolic acid prosthetic devices need to be stored from time of manufacture until time of use.

As disclosed in said U.S. Pat. No. 3,297,033, the polyglycolic acid may be formed as tubes or sheets for surgical repair and may also be spun as thin filaments and woven or felted to form absorbable sponges or absorbable gauze, or used in to form absorbable sponges or absorbable gauze, or used in conjunction with other compressive structures as prosthetic devices within the body of a human or animal where it is desirable that the structure have short-term strength, but be absorbable. The useful embodiments include tubes, including branched tubes or Tees, for artery, vein or intestinal repair, nerve splicing, tendon splicing, sheets for tying up and supporting damage kidney, liver and other intestinal organs, protecting damaged surface areas such as abrasions, particularly major abrasions, or areas where the skin and underlying tissues are damaged or surgically removed.

In more detail, the medical uses of polyglycolic acid include, but are not necessarily limited to:
1. Solid Products, molded or machined
   a. Orthopedic pins, clamps, screws and plates
   b. Clips (e.g. for vena cava)
   c. Staples
   d. Hooks, buttons and snaps
   e. Bone substitutes (e.g. mandible prosthesis)
   f. Needles
   g. Non-permanent intrauterine devices (spermocide)
   h. Temporary draining or testing tubes or capillaries
   i. Surgical instruments
   j. Vascular implants or supports
   k. Vertebral discs
   l. Extracorporeal tubing for kidney and heart-lung machines
2. Fibrillar Products, knitted or woven, including velours
   a. Burn dressings
   b. Hernia patches
   c. Absorbent paper or swabs
   d. Medicated dressings
   e. Facial substitutes
   f. Gauze, fabric, sheet, felt or sponge for liver hemostasis
   g. Gauze bandages
   h. Dental packs
   i. Sutures, including ligatures
3. Miscellaneous
   a. Flake or powder for burns or abrasions
   b. Foam as absorbable prosthesis
   c. Substituted for wire in fixations
   d. Film spray for prosthetic devices In Combination with other Components 1. Solid Products, molded or machined
   a. Slowly digestible ion-exchange resin
   b. Slowly digestible drug release device (pill, pellet)
   c. Reinforced bone pins, needles, etc.
2. Fibrillar Products
   a. Arterial graft or substitutes
   b. Bandages for skin surfaces
   c. Burn dressings (in combination with other polymeric films.)

The synthetic character and hence predictable formability and consistency in characteristics obtainable from A controlled process are highly desirable.

The most convenient method of sterilizing polyglycolic acid prostheses is by heat under such conditions that any microorganisms or deleterious materials are rendered inactive. A second common method is to sterilize using a gaseous sterilizing agent such as ethylene oxide. Other methods of sterilizing include radiation by X-rays, gamma rays, neutrons, electrons, etc., or high intensity ultrasonic vibrational energy or combinations of these methods. The present materials have such physical characteristics that they may be sterilized by any of these methods.

Strippable packages for sutures are described in U.S. Pat. Nos. 3,043,067, Rynkiewicz and Ayres, Suture Package; 2,917,878, Carnarius and Kaufman, Method of Sterile Packing and 2,949,181, Suture Package and Process of Making Same. U.S. Pat. No. 2,734,649, Callahan and Rumpf, Moistureproof Vial Closure, shows an appreciation of the type of protection required for moisture sensitive materials.

It is an object of this invention to provide a package for polyglycolic acid products which insures acceptable retention of package and in-vivo strength for prolonged periods of time even under the most undesirable conditions of temperature and humidity. It is another object of this invention to provide a method of sterilizing polyglycolic acid surgical elements using ethylene oxide.

SUMMARY OF THE INVENTION

The present invention is predicated upon the surprising and unexpected discovery that polyglycolic acid is extremely sensitive to hydrolytic attack, and that while for a period of weeks to months, depending on the temperature, may retain a high proportion of its strength, in the presence of as much as 0.5% water, based upon the weight of the polyglycolic acid; for a perferred storage life, the water or moisture content should be as low as 0.05% or less. With the small quantities of polyglycolic acid in a suture package, the total quantity of water is best described as desicated or bone dry. Exotic analytical techniques are required to detect and measure the water content.

This invention relates to a storage stable package for an absorbable sterile synthetic surgical element of a polymer subject to hydrolytic degradation to non-toxic, tissue-compatible absorbable components, such as a polyglycolic acid suture. More particularly the invention relates to a package which comprises an air tight sealed container fabricated from a material which is substantially impervious to water vapor, the container having therein said surgical element such as a polyglycolic acid suture which is substantially free from water, i.e. desiccated or bone dry. The gaseous contents of the container are, prior to sealing the container, either evacuated to yield a vacuum packaged suture or replaced with a desiccated, that is, dry gas which is nonreactive with polyglycolic acid and which is substantially free from water. A particularly suitable container material is aluminum foil.

A variety of different packaging materials was evaluated in an attempt to find a storage stable package for polyglycolic acid sutures. For example, when the suture was packaged in Saran ® (a vinyl chloride-vinylidene chloride copolymer) the suture had totally disintegrated after only 42 days storage at 100° F. and 100% relative humidity. A similar result was observed with Scotch Pak ® film. Scotch Pak ® is a laminate of polyethylene and the polymeric ester of ethylene glycol and terephthalic acid. Other package materials also failed to protect the suture from similar adverse effects.

Prior to sealing the suture within the package of this invention, it is essential that the suture be desiccated or bone dry. The suture can be desiccated and rendered bone dry by heating for a sufficient period of time to remove the water therefrom. However, it must be noted that once this water is removed, the suture cannot be allowed to contact an environment containing moisture for even a very brief period of time, since even such a brief contact can cause severe deterioration of suture package and in-vivo strength after the suture is sealed in a water impervious container and stored for a prolonged period of time. It therefore becomes necessary when a processing gap between when the suture is dried and when it is packaged is anticipated to provide for interim storage in a dry area where the possibility of contact with moisture is eliminated.

This invention also relates to a method for preparing a storage stable package containing therein a sterile polyglycolic acid suture. Such a package is prepared by inserting the suture into a container which is substantially impervious to water vapor, sterilizing the suture and container, removing substantially all of the water from the sterilized suture, and then maintaining the dried sterilized suture in a substantially dry environment until the container is to be sealed. Prior to sealing the container, the gaseous contents thereof are either evacuated or replaced with a gas which is non-reactive with polyglycolic acid and which is substantially free from moisture.

This invention also relates to a method for sterilizing an absorbable polyglycolic acid with ethylene oxide vapor without adverse effect upon the package or in-vivo strength of the suture. In accordance with this process, a non-sterile polyglycolic acid suture is contacted with a gas having as its active component ethylene oxide. The gas is maintained at a temperature of from about 70° to 90° F. The moisture content of the gas is the ambient moisture content and no additional water is added to the gas to establish any required relative humidity therein. When a non-sterile polyglyclolic acid suture is contacted with the gas described above, sterility of the suture can be achieved with a contact time of about 4 hours or more. Suitable sterilization is achieved when the pressure of the sterilizing gas is maintained at about 5 to 30 lbs. psig.

Previous gaseous ethylene oxide sterilization procedures have called for a sterilizing gas maintained at a relatively high pressure (25 psig) and high temperature (120°–130° F.). Ordinarily, a prescribed relative humidity (i.e. 50%) is achieved by adding to the gas that amount of water which is required to establish the desired relative humidity at the temperature of sterilization. Contact times of 20 hours or more are ordinarily used. In view of the aforementioned adverse effect of water, and especially of the effect of water coupled with high temperatures, upon polyglycolic acid, it becomes apparent that sterilizing polyglycolic acid sutures by such extreme conditions of pressure, temperature, relative humidity as previously used for prolonged periods of time would be most undesirable. It is known that when polyglycolic acid is contacted with water, and particularly at high temperatures, that degradation of the polymer will occur quite rapidly. The sterilization process of this invention permits polyglycolic acid sutures to be sterilized at significantly lower temperatures and pressures and shorter time cycles. Additionally, since no moisture is deliberately added to the sterilized gas and since the compounds of the sterilized gas are anhydrous, the amount of moisture present in the sterilized chamber is significantly less than would be available using prior ethylene oxide sterilization techniques. Applicant has found that polyglycolic acid sutures can be sterilized using the process of this invention without adverse effects upon the package or in-vivo properties of the suture.

DESCRIPTION OF THE PREFERRED EMBODIMENTS

Figure 1:
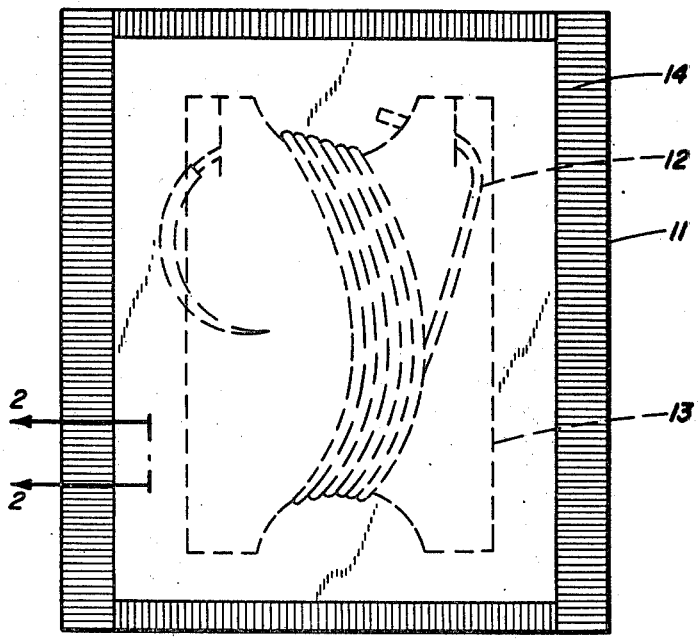
FIG. 1 is a frontal view of a preferred embodiment of the desiccated suture in the package of this invention.
Figure 2:
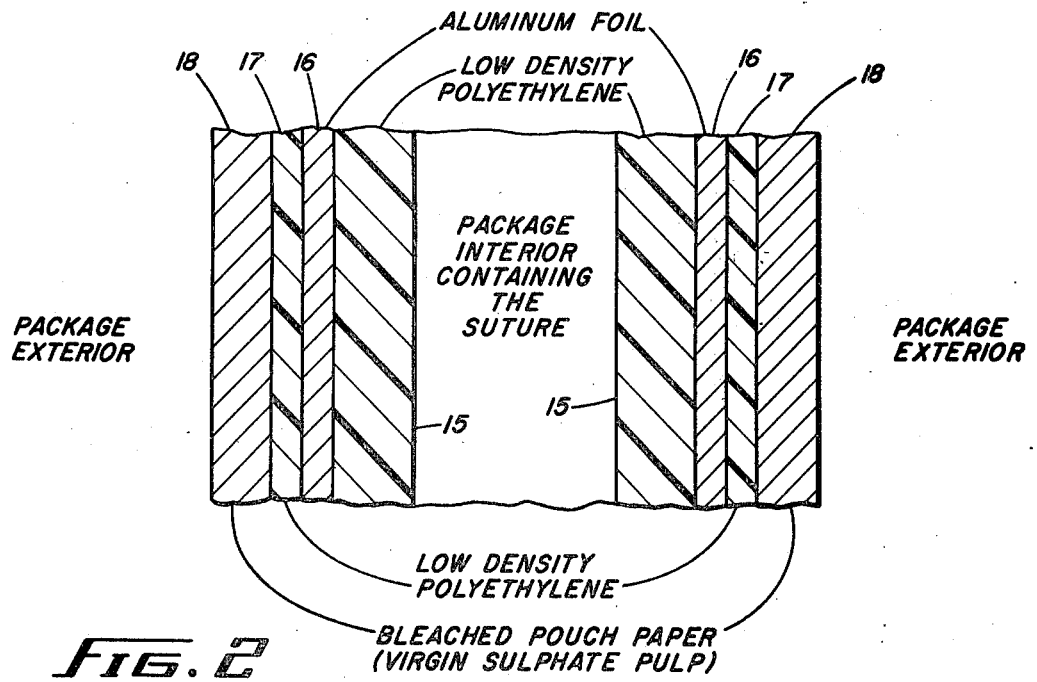
FIG. 2 is a sectional view taken along the line 2—2 of FIG. 1 and serves to illustrate the laminate structure of a preferred water impermeable container for the polyglycolic suture.

FIGS. 1 and 2 present a preferred embodiment of the package of this invention. Referring to these figures, the package comprises sealed envelope 11 containing therein sterile needled polyglycolic acid suture braid 12 wrapped around paper mounting 13. The package is sealed by peripheral heat seal 14. The material from which envelope 11 is fabricated is a four layered water impervious laminate as best seen by reference to FIG. 2. The laminate comprises a first layer 15 of heat sealable polyethylene, a second layer 16 of aluminum foil, a third layer 17 of polyethylene and a fourth layer 18 of printable paper. Envelope 11 is conveniently formed by placing two pieces of the aforementioned laminate on top of each other with heat sealable polyethylene layers 15 contacting each other. Three of the four edges are then sealed together using a standard heated die to form an envelope into which mounted suture 12 is inserted. After evacuating the contents of the envelope or replacing them with an anhydrous inert gas, the fourth edge of the envelope is sealed to produce a completely sealed package.

Polyethylene layer 15 is preferably comprised of 15 lb. low density polyethylene having a thickness of about 1.5 mils. The function of this layer is to provide a vehicle for heat sealing the package; of course, any other suitable heat sealable thermoplastic which will achieve this goal is also suitable. Examples of such other materials are Saran ®, medium and high density polyolefins, tetrafluoroethylenes, and such.

Aluminum foil layer 16 should have a thickness of at least about 0.35 mils in order to insure suitable water barrier properties with preferred thickness of about 0.35 to 1.5 mils and a highly preferred thickness of about 0.5 to 1.0 mils.

Polyethylene layer 17 preferably has a thickness of about 0.5 mils. Its function is to serve as an adhesive vehicle for joining together aluminum layer 16 and paper layer 18. Of course, any other suitable adhesive would be operable.

Paper layer 18 is preferably 25 lb. super-calendered Bleached Pouch Paper (Virgin Sulphate Pulp) having a thickness of about 1.1 mils ± 20%. The function of paper layer 18 is to permit direct printing of labels and such on the external surface of the package and hence any printable paper would be suitable.

A particularly suitable laminate of polyethylene-aluminum foil-polyethylene-paper is available from the Riegal Paper Corp., New York, N.Y., under the trade designation of Pouchpak ®.

Figure 3:
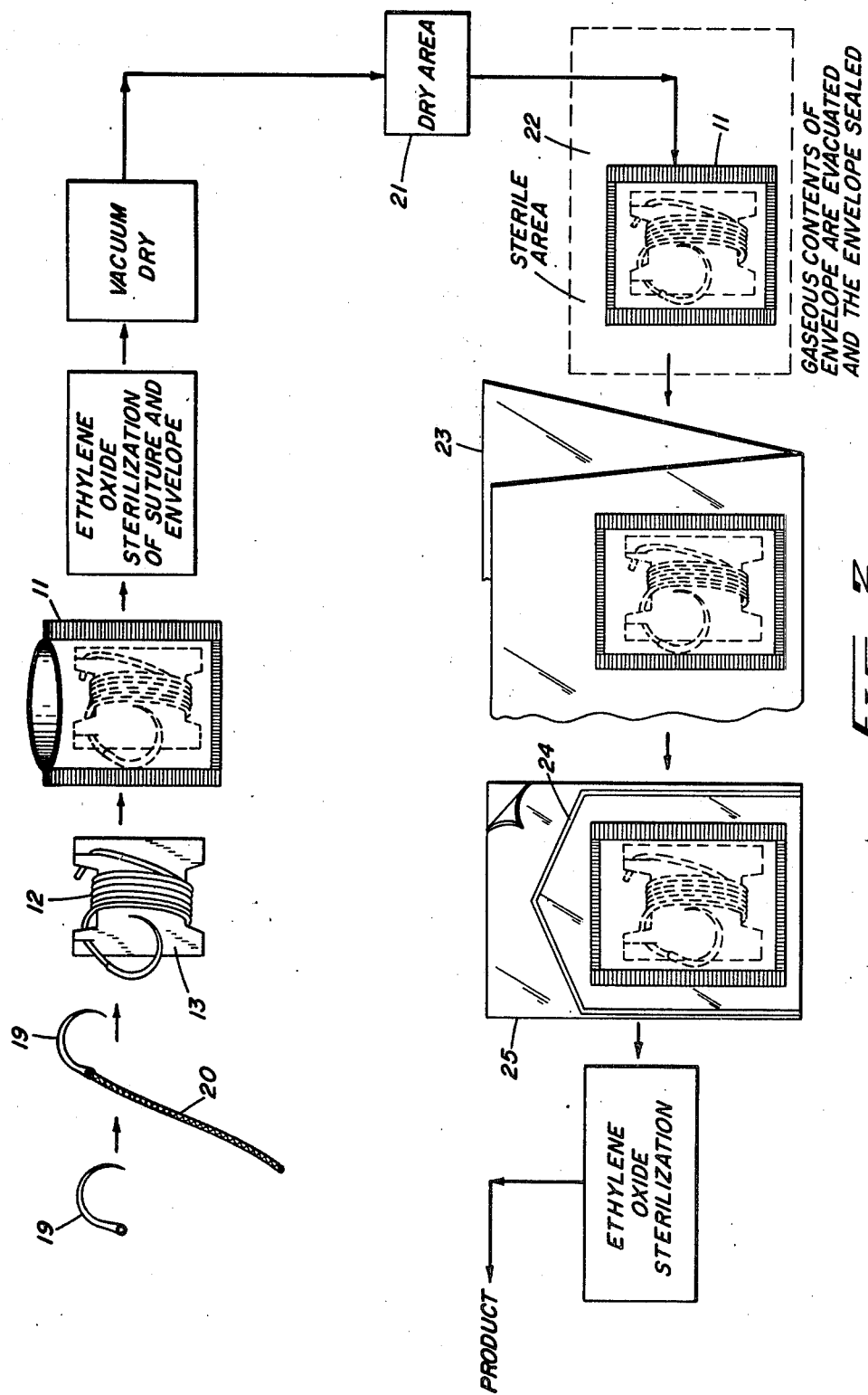
FIG. 3 is a schematic flow sheet depicting a process for preparing the storage stable polyglycolic acid suture package of this invention.

A convenient method for preparing the package of this invention is shown schematically in FIG. 3. Referring to FIG. 3, surgical needle 19 is affixed to braided polyglycolic acid suture 20 to produce needled polyglycolic acid suture braid 12. Braid 12 is then wrapped around suture mounting 13. The mounted suture is placed in envelope 11, said envelope being prepared as described above.

Envelope 11 containing mounted suture 12 is then placed within a sealed container which is permeable to sterilizing gas but not to bacteria. This container is then placed in a suitable ethylene oxide sterilizing oven. The oven is evacuated after which a mixture of 12% by volume ethylene oxide and 88% by volume dichlorodifluoromethane (Freon ® 12) is admitted to the oven. The oven pressure is raised to about 10 psig by admitting more of the gas mixture. The temperature of the gas mixture is maintained at 70°-90° F. The ethylene oxide-Freon ® mixture is non-flammable and explosion proof and is safe in all proportions when mixed with air. The Freon ® is essentially a diluent and, of course, other suitable diluents such as carbon dioxide or other members of the Freonl ® family and their mixtures are also quite suitable. The important aspect about the sterilization process is that the polyglycolic acid suture can, surprisingly, be sterilized in a relatively dry environment at low temperatures, moderate pressures, and with very brief sterilization time cycles.

After the suture has been in contact with the sterilizing mixture for at least 4 hours and preferably 8 hours, the sealed container containing suture 12 is removed from the ethylene oxide oven and placed in a dry oven whereupon it is heated at 180° to 188° F. for 1 hour under a 26 inch vacuum, thereby reducing the level of absorbed moisture to below about 3 ppm. Sterility of the suture is maintained during this drying step since bacteria cannot permeate the container surrounding suture 12. The container having suture 12 therein is then stored in a dry area 21, i.e. an environment substantially free from moisture, until the final sealing of envelope 11. At this point the bacteria proof container containing envelope 11 and suture 12 is removed from the dry area 21 and transferred into sterile area 22 whereupon envelope 11 containing suture 12 is removed from its bacteria-proof container. The gaseous contents of envelope 11 are evacuated in sterile area 22 and envelope 12 is heated sealed to produce an air-tight vacuum package polyglycolic acid suture. Alternatively in sterile area 22, the gaseous contents of envelope 11 can be replaced by an anhydrous, that is desiccated, gas which is inert towards polyglycolic acid such as $N_2$, argon, xenon, helium, $H_2$, $CO_2$, air, or the like after which envelope 11 is heat sealed to produce a non-vacuum packaged polyglycolic acid suture. Sealed envelope 11 is then removed from sterile area 22 and inserted into folded plastic sheet 23. Sheet 23 is heated sealed around envelope 11 by means of cathedral seal 24 to form outer strippable envelope 25 containing therein sealed, suture containing, inner envelope 11. A variety of materials is suitable for use as outer strippable envelope 25. For example, various plastic, paper, and metallic foil materials can be used, a preferred material being described in U.S. Pat. No. 2,949,181 which is incorporated by reference. The dual envelope suture package is then placed in an ethylene oxide (EO) oven in order to sterilize the outer surfaces of envelope 11, the inner surface of envelope 25 and the void volume defined by said surfaces. The EO vapor permeates outer envelope 25 to achieve this sterilization. The mechanics of this sterilization step are well known and are outlined in greater detail in U.S. Pat. No. 2,917,878, said patents being herein incorporated by reference. When sterilization is complete a stoage stable polyglycolic acid suture package is provided which is entirely sterile except for the outer surface of envelope 25. Such package is particularly sutiable for serving a sterile suture to a surgeon for use.

In reference to the above process, it is apparent that the sequence and nature of the process steps can be changed somewhat without effecting the nature of the finished packaged product. For example, suture 12 and envelope 11 may be separately sterilized and then assembled in sterile area 22. Alternatively, suture 12 contained in envelope 11 can be vacuum dried prior to sterilization except that, in that event, a subsequent drying step would be required if any moisture was picked up by suture in the sterilization process. Also, suture 12 can be dried priro to inserting it into envelope 11. Of course, a variety of sterilization techniques can be used such as heat sterilization, X-rays, beta or gamma radiation and such. However, the preferred method of sterilization is by gaseous ethylene oxide. Such variations in the sequence and nature of the process steps are apparent to those skilled in the art and are deemed to fail within the scope of the claims appended hereto.

The polyglycolic acid suture itself may be in any form whatsoever such as a multifilament braid or a monofilament. It may further be needled, dyed, coated, or otherwise treated in accordance with standard suture techniques.

Data are presented in Table I which indicate the effect of various storage conditions upon the package and in-vito strength of polyglycolic acid sutures stored in the package of this invention.

TABLE I

EFFECT OF VARIOUS STORAGE CONDITIONS UPON STRENGTH RETENTION OF PACKAGED POLYGLYCOLIC ACID SUTURES

| | | | Packaged Properties | | In-Vivo Properties | | | |
| | | | | | After 7 Days Implantation | | After 15 Days Implantation | |
| Storage Condition | Months Stored | Suture Size | Straight Pull(psi) | % of Original Strength Retained | Straight Pull(psi) | % of Original Strength Retained | Straight Pull(psi) | % of Original Strength retained |
|---|---|---|---|---|---|---|---|---|
| | 0 | 3-0 | 89,700 | — | 60,200 | — | 28,300 | — |
| 76° F. - 50% R.H. | 3 | 3-0 | 88,600 | 99 | 64,900 | 108 | 19,200 | 68 |
| | 6 | 3-0 | 84,500 | 95 | 64,900 | 108 | 25,000 | 88 |
| | 0 | 3-0 | 89,700 | — | 60,200 | — | 28,300 | — |
| 96° F. -Ambient R.H. | 3 | 3-0 | 93,000 | 104 | 50,950 | 85 | 13,500 | 48 |
| | 6 | 3-0 | 86,100 | 96 | 62,400 | 104 | 19,500 | 69 |
| | 0 | 3-0 | 89,700 | — | 60,200 | — | 28,300 | — |
| Warehouse | 3 | 3-0 | 93,600 | 104 | 64,900 | 108 | 17,500 | 62 |
| | 6 | 3-0 | 85,300 | 95 | 68,200 | 113 | 22,900 | 81 |
| | 0 | 3-0 | 89,700 | — | 60,200 | — | 28,300 | — |

TABLE I-continued
EFFECT OF VARIOUS STORAGE CONDITIONS UPON STRENGTH RETENTION OF PACKAGED POLYGLYCOLIC ACID SUTURES

| Storage Condition | Months Stored | Suture Size | Packaged Properties | | In-Vivo Properties | | | |
|---|---|---|---|---|---|---|---|---|
| | | | | | After 7 Days Implantation | | After 15 Days Implantation | |
| | | | Straight Pull(psi) | % of Original Strength Retained | Straight Pull(psi) | % of Original Strength Retained | Straight Pull(psi) | % of Original Strength retained |
| 132° F. - 10% R.H. | .23 | 3-0 | 87,800 | 98 | 65,700 | 109 | 24,500 | 87 |
| | .70 | 3-0 | 84,100 | 94 | 53,100 | 88 | 7,900 | 28 |
| | 1.4 | 3-0 | 79,200 | 88 | 40,800 | 68 | 1,900 | 7 |
| | 0 | 1-0 | 71,300 | — | 49,200 | — | 13,400 | — |
| 76° F. - 50% R.H. | 3 | 1-0 | 70,400 | 99 | 52,700 | 107 | 11,100 | 82 |
| | 6 | 1-0 | 71,300 | 100 | 51,200 | 104 | 13,100 | 98 |
| | 0 | 1-0 | 71,300 | — | 49,200 | — | 13,400 | — |
| 96° F. -Ambient R.H. | 3 | 1-0 | 69,800 | 98 | 52,700 | 107 | 11,100 | 83 |
| | 6 | 1-0 | 69,200 | 97 | 52,100 | 106 | 9,900 | 74 |
| | 0 | 1-0 | 71,300 | — | 49,200 | — | 13,400 | — |
| Warehouse | 3 | 1-0 | 70,800 | 98 | 52,100 | 106 | 11,900 | 89 |
| | 6 | 1-0 | 68,800 | 97 | 53,300 | 108 | 12,500 | 93 |
| | 0 | 1-0 | 71,300 | — | 49,200 | — | 13,400 | — |
| 132° F. - 10% R.H. | .23 | 1-0 | 72,100 | 101 | 50,700 | 103 | 10,950 | 82 |
| | .70 | 1-0 | 65,200 | 91 | 42,500 | 86 | 5,100 | 38 |
| | 1.4 | 1-0 | 61,900 | 87 | 24,500 | 50 | 870 | 6 |

Values are presented as the percent of the original strength retained. In reference to package properties, this terminology means that on day zero of the storage period, the package strength of a control (packaged) suture was measured. As storage time progressed, package strength (i.e., knot pull and straight pull) was measured at prescribed intervals and compared to the value of the control package strength on day zero to give a "percent of strength retained". In reference to in-vivo strength, this terminology means that a control suture (no storage time) was implanted on day zero of the storage period in a rabbit for periods of 7 or 15 days after which the rabbit was sacrificed and the suture removed. The tensile strength of the removed suture was then measured and used as a standard control. As storage progressed, sutures at prescribed storage intervals were implanted in rabbits as described above and their strength measured after 7 or 15 days. This strength was then compared to the strength observed with the control suture from day zero to give a "percent of strength retained".

The data of Table I show the effect of various storage conditions upon the package and in-vivo straight pull of a size 3-0 and 1-0 suture. The strength retention both in the case of package and in-vivo properties is generally satisfactory over all the conditions studied except at 132° F. and 10% relative humidity. The data clearly indicate the extremely rapid deterioration in suture strength to be expected even with the preferred package of this invention when the relative humidity on the outside of the package is low while the temperature on both the inside and outside of the package is high. The data also indicate that where temperatures are low but the external relative humidity is high, satisfactory storage can be achieved. An analysis of these data show that the package of this invention adequately prevents the moisture existing in either a high or low moisture environment surrounding the package from contacting the suture therein. However, as storage temperatures are raised, apid deterioration of the suture strength, and in particular the in-vivo strength of the suture, occurs despite the ability of the package to prevent the entry of moisture into the contents of the package.

Figure 4A:
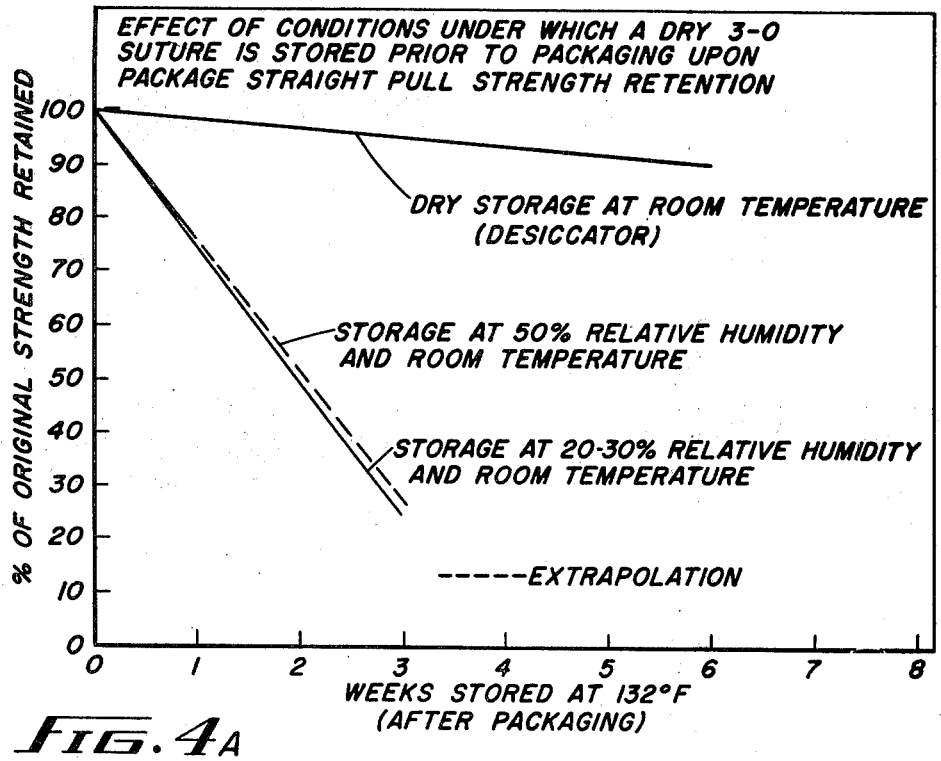
FIG. 4a shows the effect of the interim conditions which exist between drying the suture and packaging the suture in the package of this invention upon package straight pull of the suture after storage at 132° F.
Figure 4B:
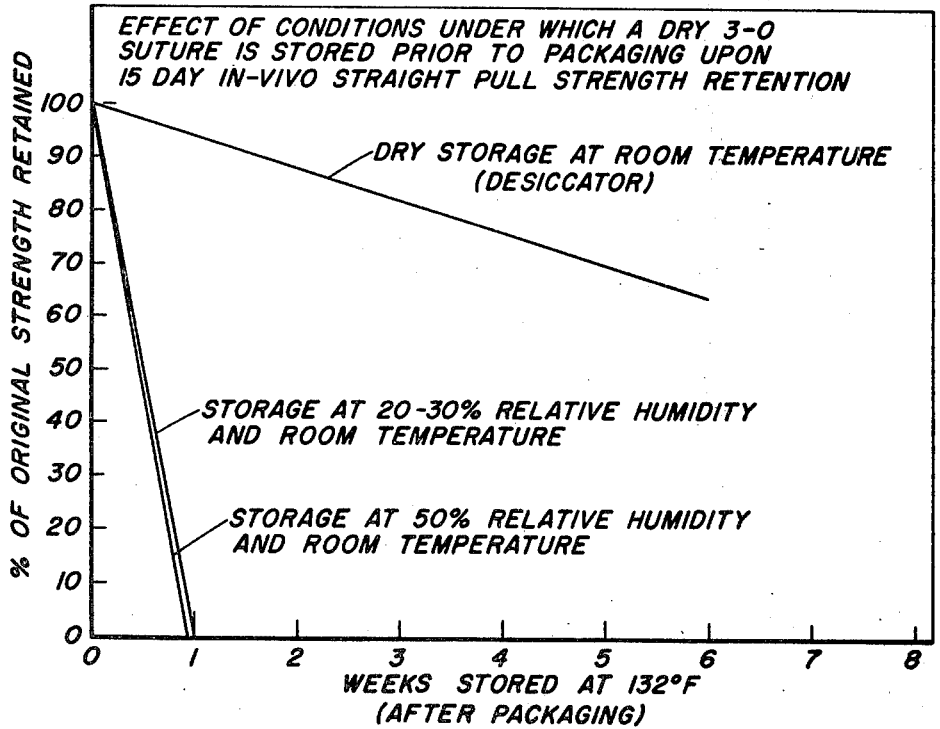
FIG. 4b shows the effect of the interim conditions which exist between drying the suture and packaging the suture in the package of this invention upon 15 day in-vivo straight pull after storage at 132° F.

Data are presented in Table II which indicate why such rapid deterioration of future properties occurs after sotrabe at 132° F. Certain of these data are presented in FIG. 4a (package straight pull) and FIG. 4b (15 day in-vivo straight pull) and clearly indicate the importance of keeping the suture dry up to the point of packaging it in the package of this invention if suture strength is to be retained during prolonged storage at elevated temperatures such as 132° F.

TABLE II.
EFFECT OF PRE-PACKAGING ENVIRONMENT UPON STRENGTH RETENTION OF PACKAGED POLYGLYCOLIC ACID SUTURES AFTER STORAGE UNDER A VARIETY OF CONDITIONS

| Storage Conditions | Weeks Stored | Condition of Suture Prior to Packaging | Suture Size | Package Properties | | | | In-Vivo Properties After 15 Day Implantation | |
|---|---|---|---|---|---|---|---|---|---|
| | | | | Straight Pull(psi) | % of Original Strength Retained | Knot Pull(psi) | % of Original Strength Retained | Straight Pull(psi) | % of Original Strength Retained |
| | 0 | | 3-0 | 71,600 | — | 48,200 | — | 7,500 | — |
| 100° F. | 1 | | 3-0 | 68,000 | 95 | 47,600 | 99 | 5,300 | 71 |
| 100% R.H. | 3 | heated at 188° F. | 3-0 | 68,000 | 95 | 42,000 | 87 | 5,100 | 68 |
| | 6 | for one hour under vacuum and then exposed for 24 hours | 3-0 | 63,400 | 88 | 46,700 | 97 | 2,900 | 39 |
| | 0 | | 3-0 | 71,600 | — | 48,200 | — | 7,500 | — |
| 132° F. | 1 | to an environment | 3-0 | 54,400 | 76 | 41,400 | 86 | 0 | 0 |
| 10% R.H. | 3 | having 50% relative | 3-93 | a | — | a | — | a | — |
| | 6 | humidity | 3-0 | a | — | a | — | a | — |
| | 0 | | 3-0 | 71,600 | — | 48,200 | — | 7,500 | — |
| 100° F. | 1 | | 3-0 | 69,300 | 97 | 47,400 | 98 | 7,800 | 104 |
| 100% R.H. | 3 | heated at 188° F. | 3-0 | 69,000 | 96 | 45,600 | 95 | 8,000 | 107 |
| | 6 | for one hour under vacuum and placed in a lever-pak containing an environment having 20-30% R.H. | 3-4,800 | 66,700 | 93 | 43,400 | 90 | 4,100 | 55 |
| | 0 | | 3-0 | 71,600 | — | 48,200 | — | 7,500 | — |
| 132° F. | 1 | | 3-0 | 60,000 | 84 | 44,200 | 92 | 235 | 3 |
| 10% R.H. | 3 | | 3-0 | 17,800 | 25 | 13,300 | 28 | 0 | 0 |
| | 6 | | 3-0 | b | — | b | — | — | — |
| | 0 | | 3-0 | 71,600 | — | 48,200 | — | 7,500 | — |
| 100° F. | 1 | | 3-0 | 68,000 | 95 | 48,600 | 101 | 4,000 | 54 |

TABLE II.-continued
EFFECT OF PRE-PACKAGING ENVIRONMENT UPON STRENGTH RETENTION OF PACKAGED POLYGLYCOLIC ACID SUTURES AFTER STORAGE UNDER A VARIETY OF CONDITIONS

| Storage Conditions | Weeks Stored | Condition of Suture Prior to Packaging | Suture Size | Package Properties | | | | In-Vivo Properties After 15 Day Implantation | |
|---|---|---|---|---|---|---|---|---|---|
| | | | | Straight Pull(psi) | % of Original Strength Retained | Knot Pull(psi) | % of Original Strength Retained | Straight Pull(psi) | % of Original Strength Retained |
| 100% R.H. | 3 | heated at 188° F. | 3-0 | 65,500 | 91 | 44,800 | 800 | 8,000 | 107 |
| | 6 | for one hour under vacuum and then | 3-0 | 65,600 | 91 | 45,600 | 95 | 10,900 | 145 |
| | 0 | immediately place | 3-0 | 71,600 | — | 48,200 | — | 7,500 | — |
| 132° F. | 1 | in a dessicator | 3-0 | 66,600 | 93 | 45,600 | 95 | 2,700 | 36 |
| 10% R.H. | 3 | until packaged | 3-0 | 65,500 | 91 | 44,800 | 93 | 5,800 | 78 |
| | 6 | | 3-0 | 65,600 | 91 | 45,600 | 95 | 4,600 | 64 | a. suture not tested due to unsatisfactory strength values after only one week storage
b. suture disintegrated and could not be tested The data of Table II detail a study of the effect of the interim conditions to which the suture is exposed between when it is dried and when it is sealed in the package of this invention. In one case, the dired suture was exposed to an environment maintained at room temperature but having 50% relative humidity for 24 hours. The envelope containing the suture was then sealed, packaged in any outer strippable envelope, and stored at 132° F. and 10% relative humidity; after only one week storage at these conditions, the suture had retained virtually no in-vivo strength while simultaneously its packaged strength had severaly deteriorated.

In another case a dried suture was stored in a container at room temperature in an environment having 20 to 30% relative humidity. The suture was then packaged as above. The same rapid deterioration in suture strength which was noted with interim storage under conditions of 50% relative humidity was also observed in this case.

In a final case, the dried suture was removed from the drying oven and immediately placed in a desiccator where it remained until sealed in its package. As can be seen from FIGS. 4a and 4b, after 6 weeks storage at 132° F., the package and in-vivo strength retention of the sutures were at satisfactory levels. Storage for one week at 32° F. and 10% relative humidity is equivlent to storage for 1 year at 72° F. and ambient humidity.

The above results are provided to clearly indicate the importance of preserving the suture in a dry state once it has been dried until it is sealed within its water-impervious package. In some cases, even very brief exposure of dried sutures to moist environmental conditions has, surprisingly, produced extremely rapid deterioration of suture strength when the sutures are subsequently packaged and stored, particularly when storage occurs under conditions of high temperature which accelerate the undesirable effect upon the polyglycolic acid suture.

Table III presents data which compares the storage capabilities of the package of this invention with those of a typical package which is in widespread use for catgut sutures under various storage conditions. The catgut package referred to is that described in U.S. Pat. No. 2,917,878.

TABLE III
COMPARISON OF THE STORAGE CAPABILITIES OF THE PACKAGE OF THIS INVENTION WITH THOSE OF A TYPICAL PACKAGE USED WITH CATGUT SUTURES.

| Packaging Material | Storage Conditions | Days Stored | Suture Material | Suture Diameter(mils) | Package Properties | | 15-Day In-Vivo Properties | |
|---|---|---|---|---|---|---|---|---|
| | | | | | Straight Pull(psi) | % of Original Strength Retained | Straight Pull(psi) | % of Original Strength Retained |
| Scotch-Pak® | 100° F.-100% R.H. | 0 | Catgut | 11.9 | 59,700 | — | 8,270 | — |
| | | 7 | | 12.6 | 57,000 | 95 | 6,100 | 74 |
| | | 14 | | 12.6 | 57,300 | 96 | 8,600 | 104 |
| | | 21 | | 12.7 | 52,900 | 89 | 3,550 | 43 |
| | | 42 | | 12.7 | 50,540 | 84 | 4,890 | 59 |
| Package of this Invention | 100° F.-100% R.H. | 0 | Polyglycolic Acid | 10.1 | 78,700 | — | 12,000 | — |
| | | 7 | | 10.2 | 75,900 | 96 | 9,700 | 81 |
| | | 14 | | 10.5 | 68,200 | 87 | 14,000 | 117 |
| | | 21 | | 10.2 | 74,700 | 95 | 6,360 | 53 |
| | | 42 | | 10.2 | 75,900 | 96 | 7,600 | 63 |
| Scotch-Pak® | 132° F.-10% R.H. | 0 | Catgut | 11.9 | 59,700 | — | 8,270 | — |
| | | 7 | | 12.7 | 50,500 | 84 | 4,250 | 51 |
| | | 14 | | 12.7 | 50,900 | 85 | 5,750 | 69 |
| | | 21 | | 12.9 | 51,300 | 86 | 1,990 | 24 |
| | | 42 | | 12.9 | 47,460 | 79 | 4,660 | 56 |
| Package of this Invention | 132° F.-10% R.H. | 0 | Polyglycolic Acid | 10.1 | 78,700 | — | 12,000 | — |
| | | 7 | | 10.2 | 75,900 | 96 | 10,700 | 88 |
| | | 14 | | 10.5 | 71,700 | 90 | 13,200 | 110 |
| | | 21 | | 10.4 | 76,600 | 97 | 8,000 | 67 |
| | | 42 | | 10.4 | 75,400 | 96 | 6,940 | 58 |

Figure 5A:
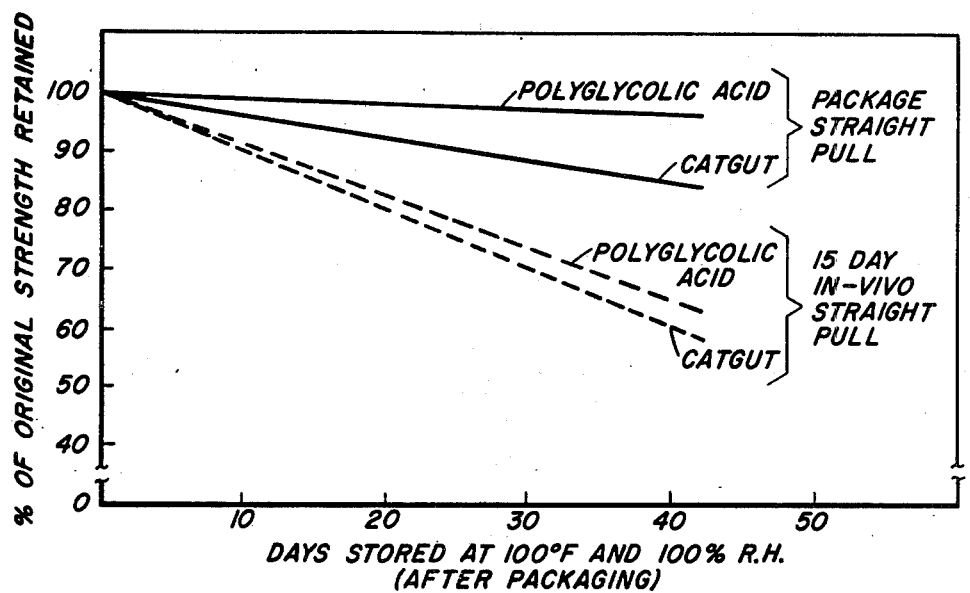
FIG. 5a compares the storage capabilities of the package of this invention with those of an acceptable catgut suture package under storage conditions of 100° F. and 100% relative humidity.
Figure 5B:
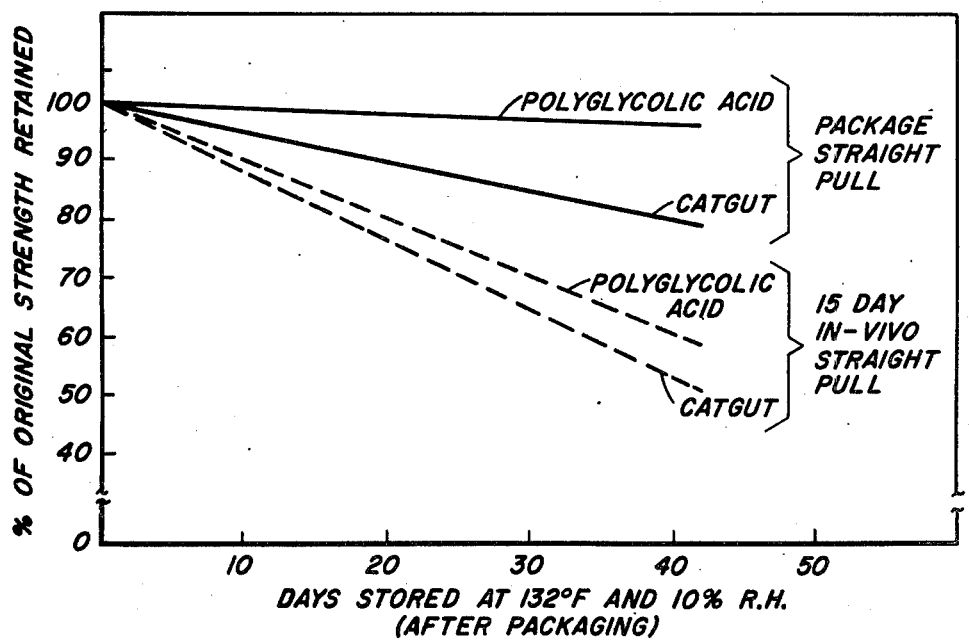
FIG. 5b compares the storage capabilities of the package of this invention with those of an acceptable catgut suture package under storage condition of 132° F. and 10% relative humidity.

The data of Table III are presented in FIGS. 5a and 5b. Referring to these Figures, it is noted that at both storage conditions studied (i.e. 100° F. — 100% relative humidity and 132° F. — 10% relative humidity), the storage capabilities of polyglycolic acid sutures with respect to both package and in-vivo strength were at least equal to that of catgut sutures and, in fact, appear to be somewhat better.

The data shown in FIGS. 5a and 5b serve to clearly indicate the ability of the package of this invention to provide prolonged stable storage of absorbable polyglycolic acid surgical sutures.

FIG. 3 shows a single moistureproof package containing a single polyglycolic suture being packaged in a single strippable outer envelope 25.

Figure 8:
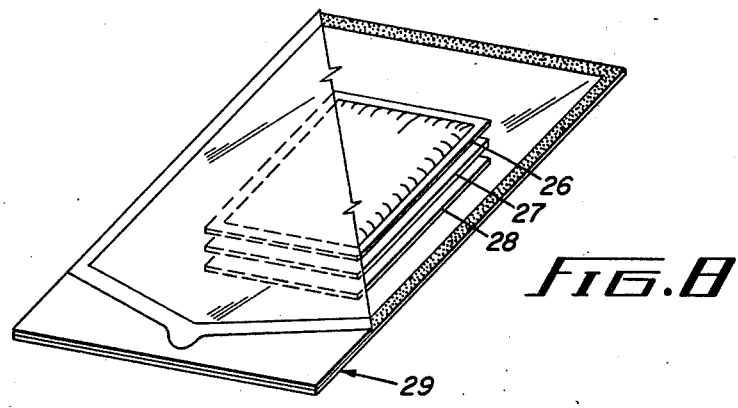
FIG. 8 shows several moistureproof envelopes packaged in an outer sterile strippable envelope.

As shown in FIG. 8, if surgical procedures consistently require severalsutures of a given size or pattern of sizes and needle types to be used at about the same time, several sealed moistureproof envelopes 26,27 and 28 containing a suture may be sealed in a sterile strippable outer envelope 29 for simultaneous transfer to a sterile operating area and release.

Figure 7:
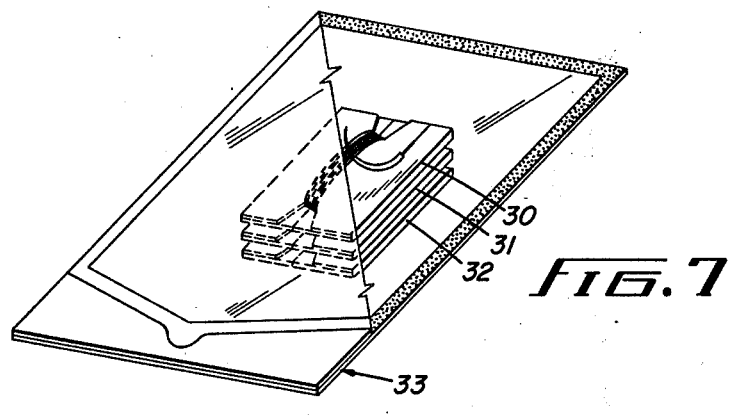
FIG. 7 shows several separate reel labels packaged in a single strippable envelope.

As shown in FIG. 7 also several individual sterile absorbably polyglycolic acid sutures, not necessarily the same size, on several reels, 30, 31, 32 may be packed in a single moistureproof envelope 33 for substantially simultaneous serving the several sutures to a surgeon. The packaging of a single suture in a single moistureproof envelope to be served from a single strippable envelope permits greater flexibility and adaptability in operating room techniques--but is by no means the only system of serving sutures to the surgeon.

For instance, three 36 inch lengths of size 2-0 polyglycolic acid braided sutures, each having a medium size ½ circle taper point needle and packaged on separate paper mountings 13, or reels, are packaged in a single sealed moistureproof envelope for surgical repair after childbirth. The group of three is often used for the surgical procedure, and can conveniently be served together. A back-up supply of other sizes, and needle configurations is available on short notice from the operating room supply as needed.

A group of three 18 inch lengths of unneedled suture braid size 3-0 are conveniently packaged together to be used as ligatures in surgery. A plurality of bleed points often requires several tie-offs.

Present operating room techniques are adapted to the presentation of a sterile inner moistureproof envelope, with release of the suture from this sterile inner envelope at time of use.

Figure 6:
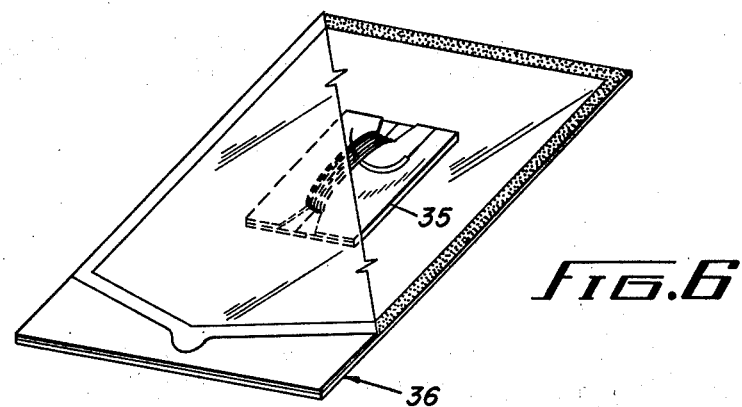
FIG. 6 shows a suture on a reel label in a single strippable envelope.

As shown in FIG. 6 another economical serving technique is for the moistureproof envelope 36 itself to be the sterile barrier, as well as the moisture barrier, with the reel-label 35 having the individual sutures wound thereon. Types of such reel-labels are shown in U.S. Pat. No. 3,357,550, Holmes & Murphy, Combination Reel and Label for Surgical Sutures, December 12, 1967. One or more such reel-labels carrying sutures permits individual sutures to be served from reels when needed, but the single envelope permits smaller packages, and economy of packaging materials. Because polyglycolic acid sutures do not require a tubing fluid, an inner envelope to hold such fluid is traditional but anachronistic, and can be eliminated, as surgical procedures in the operating room are adapted to these streamlined packaging concepts.

Whereas this invention is particularly described in reference to sutures, including ligatures, other polyglycolic acid surgical elements such as described in Schmitt and Polistina U.S. Pat. No. 3,463,158 "Polyglycolic Acid Prosthetic Devices," must be packaged in a dry environment for long term storage stability, with retention of full strength. This patent describes reinforcing elements such as fabrics for tissue reinforcement or arterial splices which consists in part of polyglycolic acid and in part of non-absorbable filaments designed for long term emplacement and retention in tissue elements.

For surgical items in which strength is not significant, dry storage is not required. For example for a glove powder, to dust surgical gloves, the material is already in powdered form, and if the powder has low strength, and is rapidly absorbed, the product is completely acceptable.

Similarly, if a surgical element, such as a heart valve, is to be used within a few days of manufacture, dry storage is not required. Also, storage at low temperatures, as for example in a refrigerator or freezer, gives longer useful life, and sutures can be stored even if not dry for a useful period if kept cool.

Usually, dry packaging to give a useful shelf life of at least three years to five years at room, shipping, and warehouse temperatures is preferred, as controlled storage conditions can add to costs.

Also it is desirable that for surgical supplies, all precautions to supply the highest standard of product under all conditions be used. Hence a product with short-term or special storage characteristics should not be used where modern packaging techniques permit greater storage stability.

A unique and unexpected additional advantage of the present moistureproof package is that the needles never rust. Carbon steel needles often rust in tubing fluid, and additives to prevent rust are sometimes used. Here the package is moixture free, and rusting on storage is no longer a problem.

An additional advantage of vacuum packaging in foil is that the outline of the suture and needle show through the foil laminate. If the foil laminate as supplied has a pinhole in it, the loss of vacuum changes the shape of the package permitting visual inspection.

Other hermetic packages can be used, such as sealed glass tubes, sealed tin cans, and the like, but such packages are more expensive and less convenient than a foil laminate package.

The determination of the moisture content of polyglycolic acid sutures in their envelopes is quite exotic. Certain samples were run in which 0.2 gram of a sample was sealed in a moistureproof envelope of the type herein described and the quantities of moisture were determined.

0.02% of moisture, based on the weight of the suture is 200 parts per million by weight and with 0.2 grams of sample, corresponds to 40 micrograms of water.

Polyglycolic acid suture braid is hygroscopic and absorbs water from its environment even during the transfer to analytical equipment to determine moisture content.

Certain analyses were made on a CEC/Analytical Instruments Division of Bell & Howell Corporation Type 26-321A Moisture Analyzer which reads to 0.1 micrograms of water on a digital readout. This device uses an electrolytic cell with a phosphorous containing electrolyte to absorb water and measures the amount of electricity required to electrolyze the absorbed water. Dry nitrogen is swept over a sample heated to 125° C., which takes up the water with the water being absorbed from the nitrogen in the electrolytic cell, which is then electrolyzed. With a suitable conversion factor this gives direct reading of the quantity of water.

Inasmuch as the polyglycolic acid itself as well as the paper label are organic, high temperatures will decompose the materials to yield water even though the water is not present as such at lower temperatures.

Results obtained appears internally consistent, and were consistent with those found by radio-tracer techniques in which the polyglycolic acid was exposed to tritiated water, for various length of time, and the water content computed from scintillation count of tritium decay.

The difficulty with accurate analysis can be illustrated by results in a test in which 0.2 gram of polyglycolic acid suture braid was transferred from the moistureproof envelope to a sample chamber for moisture analysis. With a dry braid, with the sample exposed for 5 seconds during the transfer to ambient room conditions of 48% relative humidity and 70° F., temperature, the braid absorbed 0.037% moisture. With a 15 second transfer, the braid absorbed 0.076% moisture. With an exposure of 35 minutes, the moisture rose to 0.039%. Because of the almost universal occurence of envelope and accordingly it is only the temperature which is controlling.

Table IV following shows the moisture of the test chamber in which each set of braid was dried and the approximate parts per million of water in the atmosphere at 72° F.

TABLE IV

| Sample Number | Controlled air conditions for 72 hrs. during packaging | | Size of Braid in mils | Percent moisture in packge on Braid wt. | | Package strength-Knot Pull in pounds after 56° C Storage for | | | |
|---|---|---|---|---|---|---|---|---|---|
| | % RH at 73° F. (23° C) | parts per million H₂O at 73° F. (23° C.) | | by CEC percent | by Tracer percent | Initial | 1 wk | 3 wk | 6 wk |
| A | 40 | 6900 | 13.1 | 0.53 | 0.60 | 6.4 | 2.7 | 0 | 0 |
| B | 21 | 3600 | 13.1 | 0.25 | 0.19 | 6.4 | 6.2 | 4.7 | 2.8 |
| C | 10 | 1700 | 13.0 | 0.16 | 0.14 | 6.8 | 6.95 | 6.5 | 5.7 |
| D | 3 | 500 | 12.8 | 0.05 | 0.02 | 7.0 | 6.9 | 7.0 | 6.5 |
| E | 0.15 | 30 | 13.0 | 0.02 | 0.0012 | 6.9 | 6.8 | 7.1 | 6.9 |

| Sample Number | 15 day in-vivo strength in pounds straight pull after 56° C storage for | | | |
|---|---|---|---|---|
| | Initial | 1 wk | 3 wks | 6 wks |
| A | .23 | 0 | NT | NT |
| B | .90 | .8 | 0 | 0 |
| C | 1.5 | 3.0 | .8 | 0 |
| D | 2.7 | 3.3 | 3.8 | 2.5 |
| E | 2.0 | 3.2 | 3.5 | 3.0 | moisture, and its innocuous presence under so many conditions, conditions under which its effect is deleterious are difficult to ascertain, and difficult to measure. Chemistry in a moisture free environment is indeed a rare and exotic phase of science.

A series of tests were run to determine how much moisture is absorbed by the suture braid from the ambient atmopshere, and the effect of moisture on the sutures. A group of sutures were prepared using a size 2-0 braid with a blank reel label in each envelope. In each moistureproof foil laminate envelope were placed two suture lengths of about 7 feet 2 inches to give approximately 0.2 grams of braid in each suture length, with two such lengths in each envelope. The sutures were cut, wound, tied in bundles and weighed. A group of envelopes containing sutures were placed in a fiber glass cloth sleeve, as a bacteria shield and sterilized with a 12% ethylene oxide, 88% Freon 12 mixture for 10 hours at 20 pounds gauge and ambient temperature. After sterilization, the sutures were vacuum dried for 2½ hours at a temperature of about 80° C. and less than 1 millimeter mercury total pressure. Immediately after vacuum drying, the envelopes were placed in moisture chambers at 72° F. containing the relative humidity indicated in the table. These relative humidities were chosen to use convenient salt mixtures which maintain the indicated relative humidity. The envelopes were permitted to equilibrate for 72 hours, protected by the fiber glass cloth sleeve to keep the packages sterile, after which under sterile conditions, the fiber glass cages were opened and the envelopes sealed. The sealed foiled envelopes with their moisture equilibrated contents were then packed in an outer strippable polyester-polyethylene laminate package which was sterilized through the laminate for 18 hours at 125° C. at 26 pounds gauge pressure after which the test packages were either used for immediate tests, or stored at 56° C. with ambient relative humidity for 1, 3 and 6 weeks as shown in the table. The relative humidity of the ambient conditions is essentially immaterial inasmuch as moisture does not pass into or pass out of the sealed foil As shown by Table IV, it can be seen that when the moisture content is below about 0.05% by weight of moisture based on the weight of the suture, even when stored for 6 weeks at 56° C., the sutures will maintain a good knot strength and maintains good strength on in-vivo straight pull tests. The in-vivo tests were conducted by implanting the suture in rabbits for 15 days and then removing the suture from the rabbits and determining the residual strength. With the sutures in which the interior of package was too moist, either the pull strength turned out to be essentially 0, or in some marked NT the suture had degraded so far that no test could be conducted because the suture was too weak to be emplanted in the test animal.

The above test shows that a useful degree of strength for short term storage can be obtained with as much as 0.5% moisture in the envelope but for long term storage stability, it is preferred that the moisture content be not greater than 0.05%. An even lower content of 0.02% of moisture based on the weight of the braid in the envelope gives an extra margin of safety for the storage stability of the package.

It is to be noted that the paper of the reel label can act as a moisture trap and will also hold moisture which can aid in degrading the suture if there is a comparatively high moisture content in the envelope. Where the moisture in the envelope is below about 0.5%, the amount of moisture absorbed on the label is acceptably low and does not lead to degradation of the suture. As the loss of strength is a function of the time and the moisture, the higher moisture content is acceptable where it is known that the storage life requirements are for short duration of storage only. It is preferable that the moisture content is kept below 0.05 so that the sutures in their envelopes are storage stable for a period of years, which insures sutures remaining in hospitals for a prolonged length of time before use are still good.

The 6 weeks tests at 56° C, is regarded as being equivalent to at least 3 years storage under ambient conditions which would include warehouses, shipping conditions and hospital storage and is regarded as probably equal to at least 5 years storage under such transient conditions.

Because the temperature of the storage can vary considerably, depending upon whether the suture is stored in a tropical climate such as Bombay, India, or one of the cooler Alaskan regions, the worst case must be considered as controlling in order that the suture will stand up under the worst set of conditions for a desirable length of time, at least 3 to 5 years, and will stand up under less demanding storage conditions for extended periods.

A moisture content of below about 0.05% water by weight of the polyglycolic acid braid can be considered as essentially bone dry. This permits sealing the dried suture containing envelopes at a relative humidity of about 2.5% at 72° F., which corresponds to about 450 parts per million of water in the air. A preferred operating range is about 50 parts per million, so that even if complete equilibration is not attained, the sutures are storage stable for a least 5 years. In general, the lower the level the absorbed moisture vapor is reduced to the better. Obviously, practical consideration such as the availability and cost of vapor removing equipment and means for avoiding recontamination place limitations upon this generalization. Thus, moisture levels below about 300 ppm or 0.03% such as those set forth in Table V below, are even more peferred.

Following equilibration for about 2—3 days at 50% RH and room temperature, the test suture materials set forth in Table V below were dried under a 26 inch vacuum for 1 hour at about 180°-188° F. The moisture level produced was determined in an automatic Bell and Howell Model 26 321A moisture analyzer using CEC analytical conditions of 125° C. and 25 minutes. The results are set forth below.

TABLE V

| Polyglycolic Acid Suture | | Moisture Level |
|---|---|---|
| m Glycolide/m Lactide | Construction | % |
| 100/0 | 2/0 Braid | 0.03 |
| 100/0 | 4/0 Monofil | 0.01 |
| 90/10 | 2/0 Braid | 0.02 |

In accordance with the usage set up by the Federal Trade Commission, and set forth in Title 16 of the Code of Federal Regulations, pages 462 and 463 of the 1972 edition, fibers are generally classified with the generic name if they contain over 85% content of one monomer. Here the term polyglycolic acid indicates at least 85 mol percent glycolic acid linkages. The term homopolymeric polyglycolic acid is used herein where it is intended to exclude polymers modified by incorporation of a small amount of a comonomer.

As the package strength characteristics approximate the inherent viscosity of the polymer, it is often convenient to measure the inherent viscosity of polymers in powdered form rather than extruding and spinning to form a fiber and sutures.

Good surgical elements are obtainable if the inherent viscosity is at least about 0.4. Very high grade sutures are obtained is the inherent viscosity of the polymer is at least about 1.0. Polymers with an inherent viscosity of about 1.4 are hard to spin, as extrusion requires extremely high pressures, but make a superior quality of suture with very good 21 day strengths on implantation.

Tests were run on a group of polymers of about the same inherent viscosity, with varying ratios of moles of glycolide to moles of lactide. The following Table VI shows the inherent viscosity after the listed number of days when the polymer in powdered form was stored in either sealed envelopes, or opened envelopes at a temperature of 100° F. and relative humidity of 100%.

TABLE VI

| Time Days | | INHERENT VISCOSITY - AFTER 100° F-100% R.H. EXPOSURE | | | | |
|---|---|---|---|---|---|---|
| | | F | G | H | J | K |
| — | m Glycolide/ M lactide | 100/0 | 95.8/4.2 | 87.0/13.0 | 83.2/16.8 | 81.2/18.8 |
| | Initial IV | 0.42 | 0.51 | 0.42 | 0.44 | 0.44 |
| | Sealed Envelope | .41 | .51 | .42 | .44 | .42 |
| 3 | Open Envelope | .34 | .41 | .35 | .37 | .35 |
| | % Retained | 82.3 | 79.9 | 83.3 | 84.1 | 82.0 |
| | Sealed Envelope | .41 | .51 | .42 | .44 | .42 |
| 5 | Open Envelope | .29 | .34 | .29 | .32 | .29 |
| | % Retained | 70.7 | 66.7 | 69.1 | 72.7 | 69.1 |
| | Sealed Envelope | .41 | .52 | .42 | .44 | .42 |
| 7 | Open Envelope | .24 | .23 | .23 | .24 | .24 |
| | % Retained | 58.1 | 44.8 | 54.8 | 54.6 | 56.3 |
| | Sealed Envelope | .41 | .52 | .42 | .44 | .42 |
| 15 | Open Envelope | .14 | .15 | .13 | .15 | .14 |
| | % Retained | 33.3 | 28.9 | 31.0 | 33.3 | 32.6 |
| | Sealed Envelope | .41 | .52 | .42 | .45 | .42 |
| 21 | Open Envelope | .093 | .097 | .099 | .098 | .095 |
| | % Retained | 22.7 | 18.7 | 23.6 | 21.8 | 22.6 |

As can be seen from the data, the longer the storage in open envelopes, the more the polymer is degraded, the less satisfactory the suture characteristics.

Animal implantation tests on sutures made from such polymers confirm the pattern.

In general, any exposure to moisture vapor tends to degrade the polymer, causing lower strength, and more rapid absorption.

When protected by the packages of this invention and kept dry, a storage life of at least five years under all reasonable commercial storage conditions is to be expected. If during processing and storage, the sutures are permitted to stand with absorbed moisture, the storage life is decreased, and the in vivo strength is reduced.

Obviously, for uses which do not require strength, such as a surgical powder, storage requirements are less figorous. Where strength is desired, moisture is to be excluded and bone dryness for storage is preferred for all products in which hydrolytic degradation of glycolic acid ester linkages results in tissue absorption. The present package maintains such dryness for at least several years.

Obviously, equipment for use in the practice of the present invention can be secured in a variety of designs and from a variety of sources. For laboratory scale vacuum sealing operations, the POPULAR model Swissvac sealer can be employed. Larger automated equipment will be desired for commercial packaging operations. The sealing units should be housed in a desiccated atmosphere. A stream of dried air is adequate for this purpose. Compressed air passed through a drying tower or a silica gel bed is sufficient. Its dew point should be lowered to the moistured level strived for in the surgical elements. The vacuum drying cycle is preferably broken with the dried (about 10 ppm) air which is then used to protect the packaging system through sealing. A 1 hour 180° F 26 inch vacuum drying cycle is adequate although lower vacuums (e.g. down to 1 mm or lower) may be used. Drying oven temperatures may satisfactorily range from 140° F. to 200° F.

I claim:

1. A package comprising an air-tight sealed container fabricated from a material which is substantially impervious to water vapor, said container having therein a storage stable sterile synthetic surgical element of a polymer subject to hydrolytic degradation to non-toxic, tissue-compatible absorbable components, said polymer having glycolic acid ester linkage, said storage stable sterile synthetic surgical element further characterized in that the absorbed water moisture in the sterile surgical element (in the sterile enclosure is less than 0.5% by weight of the sterile surgical element) is at or less than 0.25% by weight of the sterile surgical element, in the sterile enclosure.

2. The package of claim 1 wherein the surgical element is a polyglycolic acid suture an the vapor impervious material comprises an aluminum foil layer.

3. The package of claim 2 wherein the mositure level in said suture is up to about 0.16 percent by weight of said suture.

4. The package of claim 2 wherein the moisture level in said suture is not greater than 0.05 percent by weight of said suture.

5. The package of claim 2 wherein the moisture content in said suture is below about 0.03 percent by weight of said suture.

6. The package of claim 3 wherein the moisture content of said suture is below about 0.02 percent by weight of said suture.

7. The package of claim 2 wherein said container comprises a laminate structured as follows:
(a) a heat sealable thermoplastic layer, said layer forming at least a portion of the inner surface of the container, said inner surface being that surface adjacent to said surgical element,
(b) an aluminum foil layer about 0.35 to 1.5 mils thick adjacent to said thermoplastic layer,
(c) an adhesive layer and,
(d) a paper outer layer adjacent said adhesive layer, said outer layer being that layer exposed to the environment surrounding said package, and being bonded to said foil layer by said adhesive layer.

8. The package of claim 7 wherein the composition and thicknesses of said layers are as follows:
polyethylene layer (a): about 1.5 mils
aluminum foil layer (b): about 0.5 mil
polyethylene layer (c): about 0.5 mil
paper layer (d): about 1.1 mils ± 20%

9. The package of claim 1 wherein the surgical element is a polyglycolic acid suture and the gaseous contents of said container have been replaced with an anhydrous gas which is inert towards polyglycolic acid.

10. The package of claim 9 wherein the vapor impervious material comprises an aluminum foil layer.

11. The package of claim 10 wherein the mositure level in said suture is up to about 0.16 percent by weight of said suture.

12. The package of claim 10 wherein the moisture level in said suture is not greater than 0.05 percent by weight of said suture.

13. The package of claim 12 wherein the moisture content of said suture is below about 0.03 percent by weight of said suture.

14. The package of claim 10 wherein said container comprises a laminate structured as follows:
(a) a heat sealable thermoplastic layer, said layer forming at least a portion of the inner surface of the container, said inner surface being that surface adjacent to said surgical element,
(b) an aluminum foil layer about 0.35 to 1.5 mils thick adjacent to said thermoplastic layer,
(c) an adhesive layer and,
(d) a papper outer layer adjacent said adhesive layer, said outer layer being that layer exposed to the environment surrounding said package, and being bonded to said foil layer by said adhesive layer.

15. The package of claim 14 wherein the composition and thicknesses of said layers are as follows:
polyethylene layer (a): about 1.5 mils
aluminum foil layer (b): about 0.5 mil
polyethylene layer (c): about 0.5 mil
paper layer (d): about 1:1 mils ± 20%.

UNITED STATES PATENT OFFICE
CERTIFICATE OF CORRECTION

Patent No. 4,135,622   Dated January 23, 1979

Inventor(s) ARTHUR GLICK

It is certified that error appears in the above-identified patent and that said Letters Patent are hereby corrected as shown below:

Column 22 line 47 delete "1:1 mils" and add -- 1.1 mils --

Column 21, line 21, delete "linkage" and add -- linkages--

Signed and Sealed this

Eighteenth Day of March 1980

[SEAL]

Attest:

SIDNEY A. DIAMOND

Attesting Officer   Commissioner of Patents and Trademarks

UNITED STATES PATENT AND TRADEMARK OFFICE
CERTIFICATE OF CORRECTION

PATENT NO. : 4,135,622

DATED : January 23, 1979

INVENTOR(S) : Arthur Glick

It is certified that error appears in the above-identified patent and that said Letters Patent is hereby corrected as shown below:

Column 21, lines 24 to 25 delete "(in the sterile enclosure is less than 0.5% by weight of the sterile surgical element)"

Signed and Sealed this

Sixth Day of February, 1990

*Attest:*

JEFFREY M. SAMUELS

*Attesting Officer*   *Acting Commissioner of Patents and Trademarks*